US00PP25705P3

(12) United States Plant Patent
Fyfe

(10) Patent No.: US PP25,705 P3
(45) Date of Patent: Jul. 14, 2015

(54) *PITTOSPORUM TENUIFOLIUM* PLANT NAMED 'SILVER BALL'

(50) Latin Name: *Pittosporum tenuifolium*
Varietal Denomination: Silver Ball

(71) Applicant: Plant Production Limited, Napier (NZ)

(72) Inventor: Mark Nelson Fyfe, Hastings (NZ)

(73) Assignee: Plant Production Limited, Napier (NZ)

( * ) Notice: Subject to any disclaimer, the term of this patent is extended or adjusted under 35 U.S.C. 154(b) by 116 days.

(21) Appl. No.: 13/986,624

(22) Filed: May 20, 2013

(65) Prior Publication Data

US 2014/0345014 P1 Nov. 20, 2014

(51) Int. Cl.
*A01H 5/00* (2006.01)

(52) U.S. Cl.
USPC ..... Plt./234

(58) Field of Classification Search
USPC ..... Plt./234
CPC ..... A01H 5/00; A01H 5/02
See application file for complete search history.

(56) References Cited

PUBLICATIONS

Upov Pluto Plant Variety Database 20141030, retrived on Nov. 3, 2014, retrieved from the Internet at <www3.wipo.int/pluto/user/en/index.jsp> one page.*

* cited by examiner

*Primary Examiner* — June Hwu

(57) ABSTRACT

A *Pittosporum tenuifolium* plant particularly distinguished by grey green leaves with irregular white margins; compact and spherical plant form; vigorous growth habit and freely basal branching habit, a dense and bushy plant.

4 Drawing Sheets

Genus and species: *Pittosporum tenuifolium.*
Variety denomination: 'Silver Ball'.

BACKGROUND OF THE INVENTION

The present invention relates to a new and distinct cultivar of *Pittosporum tenuifolium* hereinafter referred to by the cultivar name 'Silver Ball' or the 'new plant'. 'Silver Ball' is a spontaneous sport from *Pittosporum tenuifolium* 'Golf Ball' (U.S. Plant Pat. No. 15,329); discovered and selected by the inventor in an ornamental plant nursery in Napier, Hawkes Bay, New Zealand in August 2008; and propagated from soft wood cuttings in the same nursery.

The new plant has been asexually propagated by softwood cuttings and the unique characteristics of the new plant have been found to be reproducible and stable in successive generations of asexually reproduced plants. The resultant plants have been found to be identical to the original selection.

Plant Variety Rights application for 'Silver Ball' was filed in New Zealand on 12 Sep. 2012 and assigned application number SHM319. 'Silver Ball' has not been sold or made publicly available, more than one year prior to the filing of this application.

SUMMARY OF THE INVENTION

The following are the most outstanding and distinguishing characteristics of the new plant when grown under normal horticultural practices in Napier, New Zealand:

1. Grey green leaves with irregular white margins
2. Compact and spherical plant form
3. Vigorous growth habit
4. Freely basal branching habit, a dense and bushy plant

DESCRIPTION OF THE PHOTOGRAPHS

The new plant is illustrated by the accompanying photographs which show the plant habit and foliage of the plant. The colors shown are as true as can be reasonably obtained by conventional photographic procedures.

The photographs are of a plant approximately 24 months old, after planting in optimum conditions in Napier, New Zealand.

Figure 1:
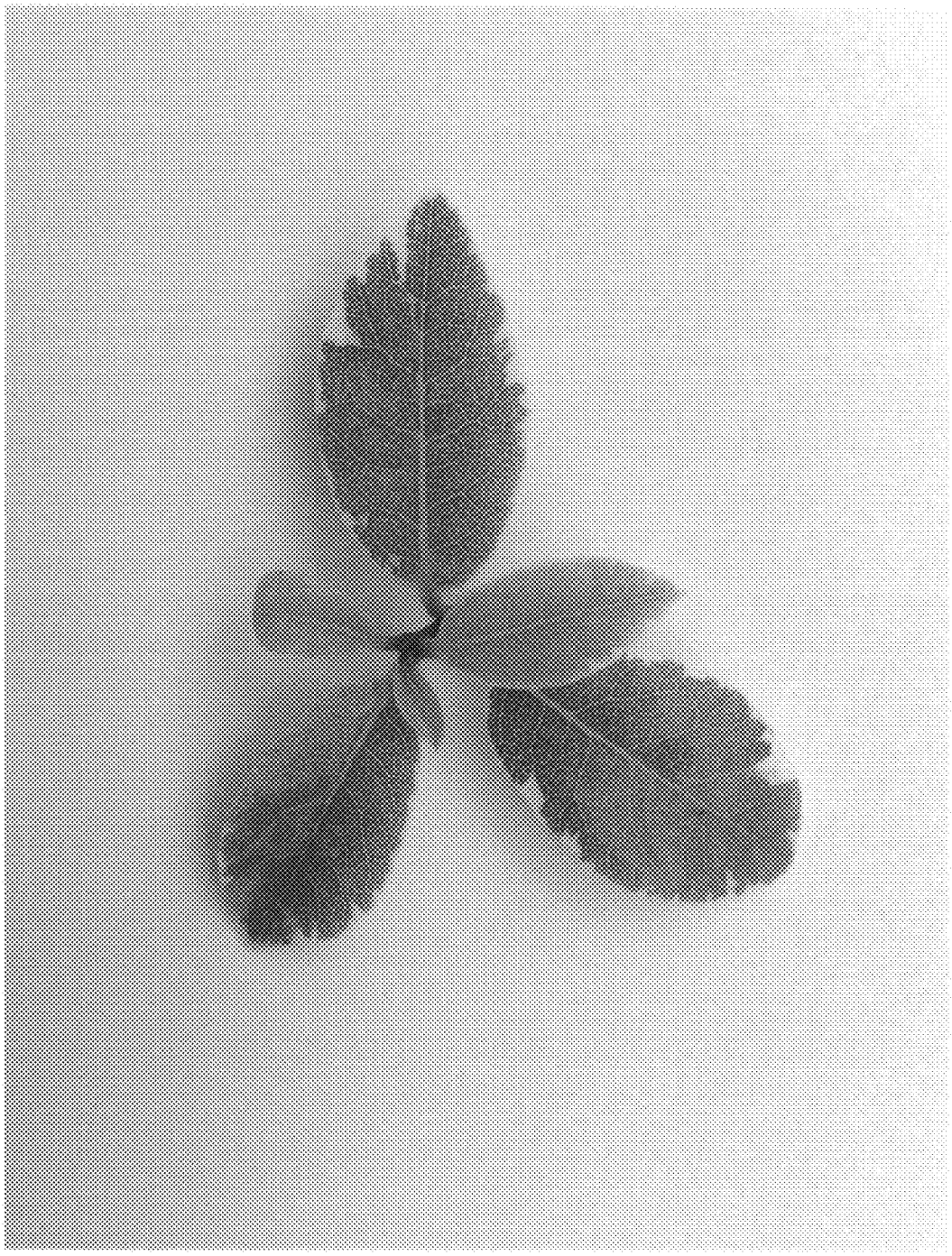
Figure 2:
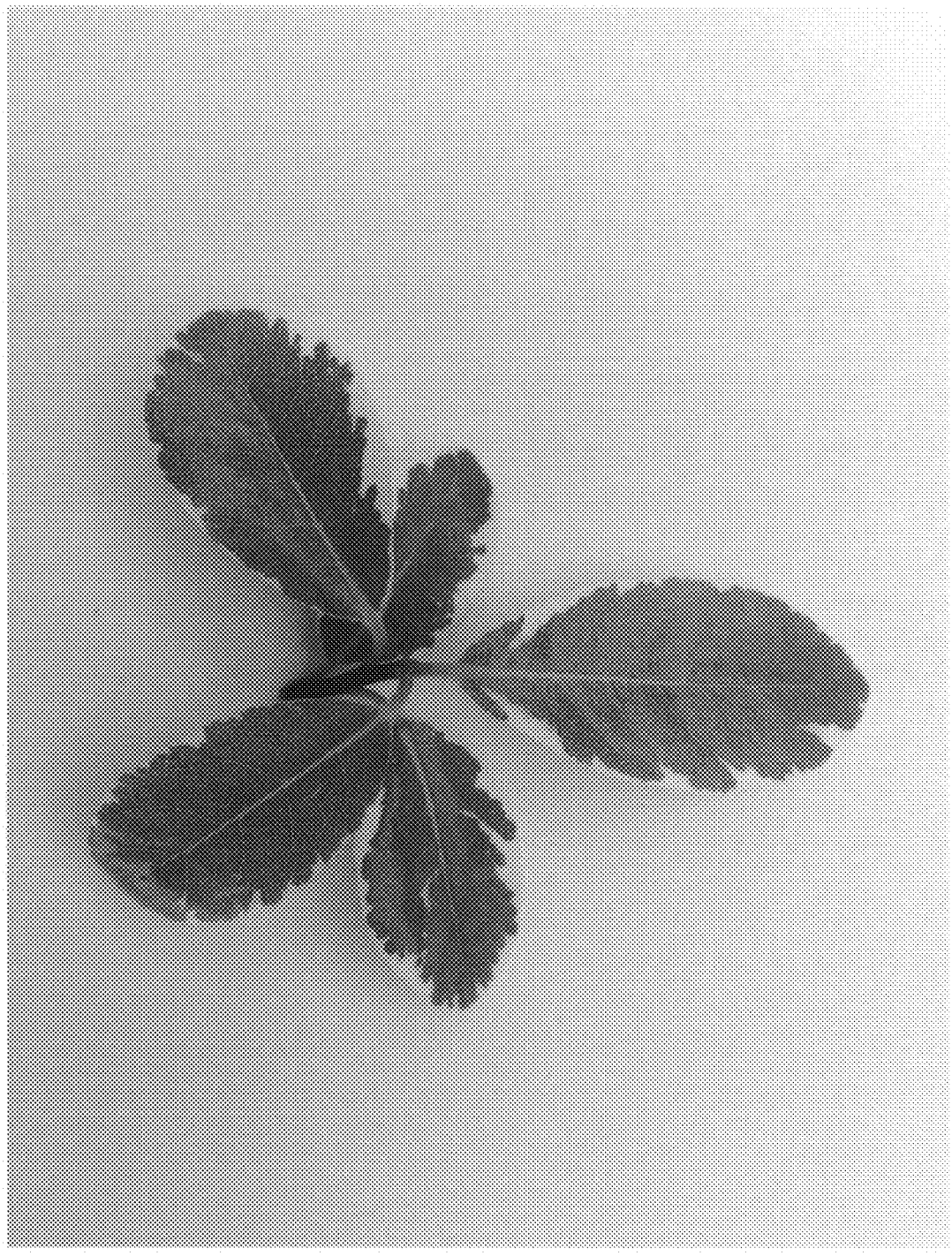
Figure 3:
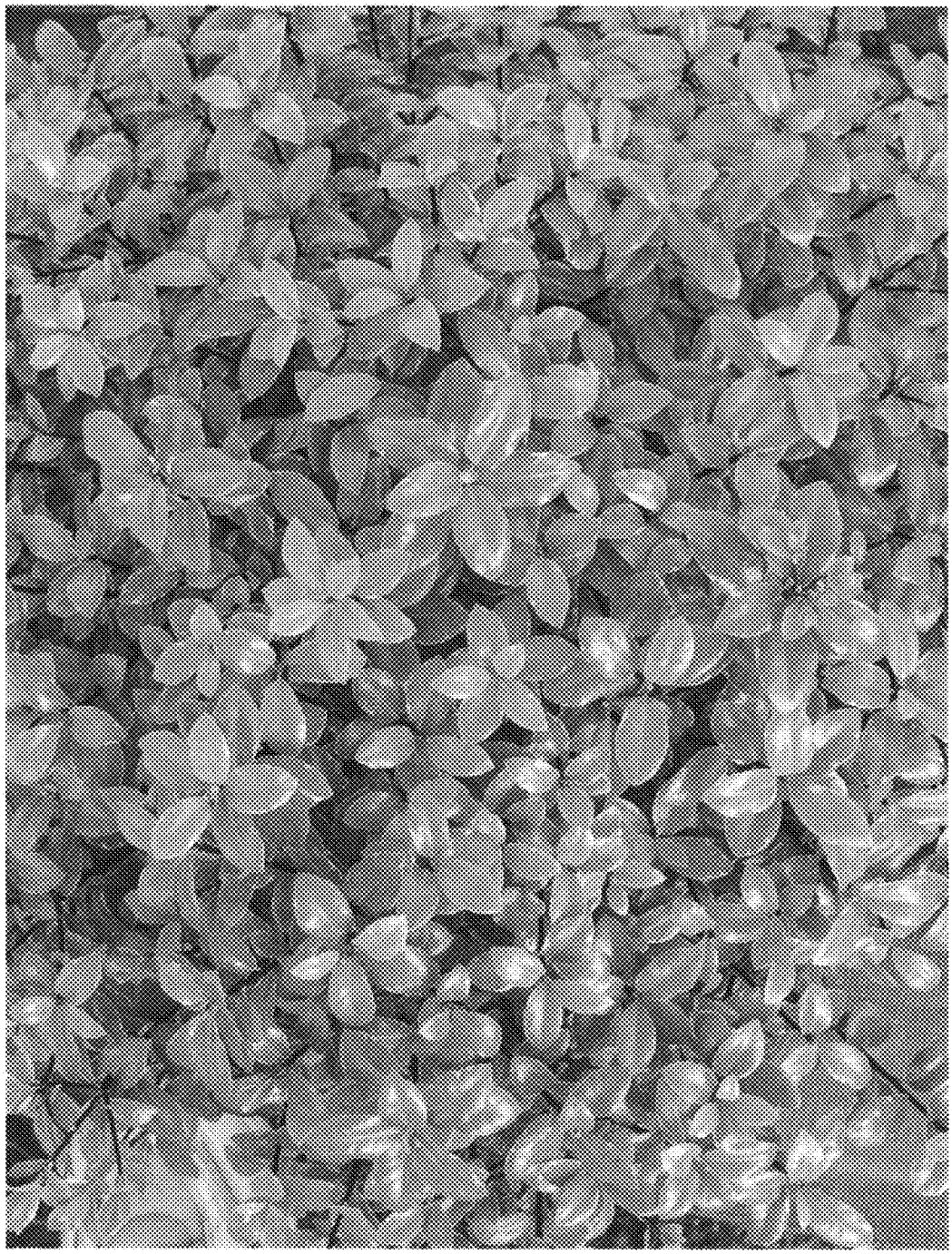
Figure 4:
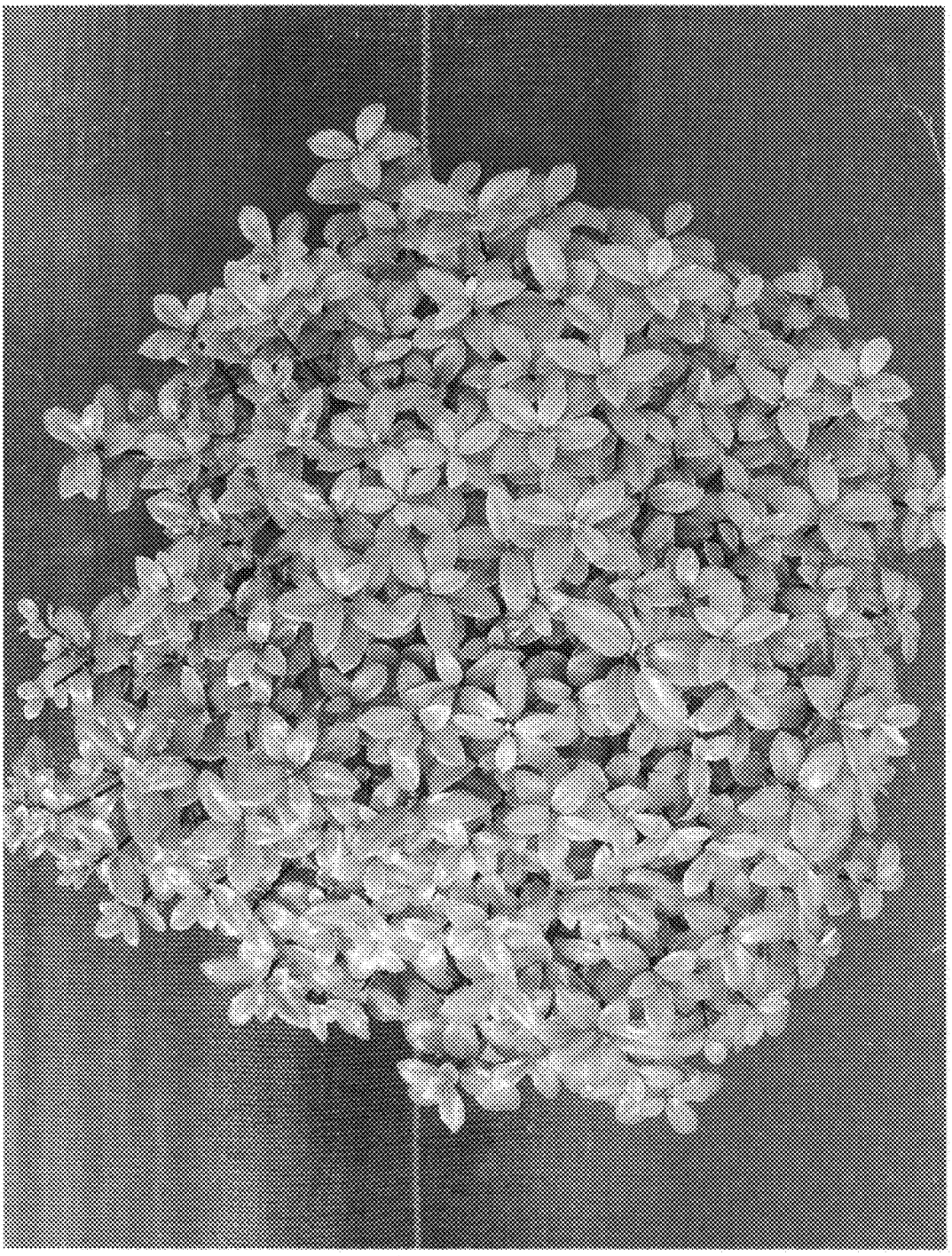

FIG. 1 shows a close-up of typical young leaves
FIG. 2 shows a close-up of typical mature leaves
FIG. 3 shows the mature foliage.
FIG. 4 shows the a typical plant grown in a container, top view

DESCRIPTION OF THE NEW CULTIVAR

The following detailed description sets forth the distinctive characteristics of 'Silver Ball'. The following observations, measurements and values describe the new cultivar at 24 months of age as grown in an outdoor nursery in Napier, New Zealand under conditions which closely approximate those generally used in commercial practice. During the production of the plants, day temperatures ranged from 10 degrees Celsius to 32 degrees Celsius and night temperatures ranged from 0.1 degrees Celsius to 15 degrees Celsius. Plants were grown in 170 mm containers and very lightly pruned to maintain the plant's symmetry.

Colour readings were taken under natural light. Color references are primarily to The 1995 Edition of The Colour Chart of The Royal Horticultural Society of London (R.H.S.), except where general colors of ordinary significance are used.

DETAILED BOTANICAL DESCRIPTION

Classification:

*Family*.—Pittosporaceae.

*Botanical name*.—*Pittosporum tenuifolium*.

*Common name*.—*Pittosporum*.

Parentage: A spontaneous sport from *Pittosporum tenuifolium* 'Golf Ball' (U.S. Plant Pat. No. 15,329).

Plant type: Evergreen perennial shrub.

Plant form: Compact spherical plant with a dense and bushy branching habit, and moderately vigorous growth.

Growth habit:

*Height* (*measured from top of the soil*).—20 cm to 30 cm.

*Diameter or area of spread*.—30 to 35 cm.

*Propagation*.—Softwood cuttings.

*Time to initiate roots, summer*.—About 34 days at 21 degrees Celsius.

*Time to initiate roots, winter*.—About 48 days at 15 degrees Celsius.

*Time to produce a rooted liner* (*young plant*).—220 days (summer); 270 days (winter).

*Rooting habit*.—Sparse roots system devoid of any hairs containing a certain amount of resin.

Branches:

*Number of primary branches per plant*.—15 to 20.

*Primary branch length*.—20 cm to 30 cm.

*Primary branch diameter*.—3 mm to 7 mm.

*Lateral branch length*.—15 cm.

*Lateral branch diameter*.—1 mm to 2 mm.

*Internodal length*.—About 5 mm.

*Texture*.—Smooth, glabrous.

*Color*.—Brown, RHS 200A.

Leaves:

*Arrangement*.—Alternate.

*Color*.—Young leaves upper surface: yellow-green, RHS 146C. Young leaves lower surface: yellow-green, RHS 145C. Mature leaves upper surface: greyed-green, RHS 191A. Mature leaves upper surface (margin): white, RHS 155A. Mature leaves lower surface: greyed-green, RHS 191B. Mature leaves lower surface (margin): white, RHS 155A.

*Length*.—2 cm to 3.5 cm.

*Width*.—0.9 cm to 1.5 cm.

*Shape*.—Elliptical.

*Apex*.—Broadly acute.

*Base*.—Attenuate.

*Margin*.—Entire.

*Texture*.—Smooth and glabrous on upper and lower surface, no pubescence.

*Quantity*.—8 to 20 leaves per lateral branch.

*Venation pattern*.—Reticulate.

*Venation color* (*upper surface*).—Base of main vein yellow-green RHS 145B; other veins greyed-green 191A.

*Venation color* (*lower surface*).—Greyed green RHS 191B.

Petioles (leaf stem):

*Length*.—2 mm to 4 mm.

*Diameter*.—1 mm to 1.5 mm.

*Texture*.—Glabrous.

*Colour*.—Yellow-green RHS 145A.

Inflorescence: No observations made.

Reproductive organs: No observations made.

Seeds and fruit: No observations made.

Disease resistance/susceptibility: No observations made.

Insect resistance/susceptibility: No observations made.

COMPARISON WITH PARENTAL AND KNOWN CULTIVARS

When compared to the commercial variety 'Elfin' (U.S. Plant Pat. No. 21,822) 'Silver Ball' has grey green leaves with irregular white margins, whereas 'Elfin' has light green leaves.

When compared to the commercial variety 'Little Burger' (unpatented); 'Silver Ball' is more symmetrical and sphere shaped and has grey green leaves with irregular white margins, whereas 'Little Burger' has a flatter, spreading habit and mid green leaves.

When compared to the parent sport 'Golf Ball' (U.S. Plant Pat. No. 15,329); 'Silver Ball' has grey green leaves with irregular white margins, whereas 'Golf Ball' has dark green leaves.

I claim:

1. A new and distinct cultivar of *Pittosporum tenuifolium* plant as shown and described herein.

* * * * *